(12) United States Patent
Terrett et al.

(10) Patent No.: US 6,187,908 B1
(45) Date of Patent: Feb. 13, 2001

(54) TUBBY 2 POLYPEPTIDES

(75) Inventors: Jonathan Alexander Terrett, Chelmsford; Tania Tamson Testa; Israel Simon Gloger, both of London; Stephen A. Hughes, Welwyn Garden City; Trudy Rachel Doe, Ware, all of (GB)

(73) Assignee: SmithKline Beecham, P.L.C. (GB)

( * ) Notice: Under 35 U.S.C. 154(b), the term of this patent shall be extended for 0 days.

(21) Appl. No.: 08/977,865

(22) Filed: Nov. 25, 1997

(30) Foreign Application Priority Data

Nov. 25, 1996 (GB) .................................. 96 24433
Oct. 6, 1997 (EP) ................................. 97 307877

(51) Int. Cl.⁷ ..................................... C07K 1/00
(52) U.S. Cl. ........................ 530/350; 530/351; 530/399; 530/395; 514/2; 514/8; 514/12; 514/909
(58) Field of Search ................... 530/350, 395, 530/399; 930/120; 514/2, 8, 12, 909

(56) References Cited

U.S. PATENT DOCUMENTS

| | | | | |
|---|---|---|---|---|
| 5,646,040 | * | 7/1997 | Kleyn et al. | 435/325 |
| 5,770,432 | * | 6/1998 | Nishina et al. | 435/252.3 |
| 5,776,762 | * | 7/1998 | North et al. | 435/252.3 |
| 5,817,762 | * | 10/1998 | Kleyn et al. | 530/350 |
| 6,114,502 | * | 9/2000 | North et al. | 530/350 |

FOREIGN PATENT DOCUMENTS 97309380    3/1998  (EP) .
WO 96/05861  2/1996  (WO) .

OTHER PUBLICATIONS

Kleyn, P.W., "Identification and Characterization of the Mouse Obesity Gene *tubby* A Member of a Novel Gene Family", Cell, vol. 85, pp. 281–290 (1996).
Weigle, D.S., "Obesity genes and the regulation of body fat content", BioEssays, vol. 18 (11), pp. 867–874 (1996).
Coleman et al. J. Heredity, 1990, vol. 81(6) p. 424.*
Nobren Irauth et al, Nature, 380, 1996, p. 534.*

* cited by examiner

*Primary Examiner*—Garnette D. Draper
(74) *Attorney, Agent, or Firm*—William T. Han; Ratner & Prestia; William T. King

(57) ABSTRACT

Tubby 2 polypeptides and polynucleotides and methods for producing such polypeptides by recombinant techniques are disclosed. Also disclosed are methods for utilizing Tubby 2 polypeptides and polynucleotides in the design of protocols for the treatment of diabetes, obesity, and atherosclerosis, among others, and diagnostic assays for such conditions.

14 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1180 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGAAGATGC GACAGGCTAA GCTGGATTAT CAGAGGCTAC TACTTGAGAA GAGGCAAAGG      60

AAAAAGCGCC TTGAGCCATT TATGGTGCAG CCCAATCCAG AAGCCAGGCT ACGTCGGGCA     120

AAGCCAAGGG CCAGTGATGA GCAGACTCCC TTGGTGAACT GTCATACTCC CCACAGCAAT     180

GTCATCTTAC ATGGTATTGA TGGTCCAGCT GCTGTCCTGA AACCAGACGA AGTTCATGCT     240

CCATCAGTAA GCTCCTCTGT TGTGGAAGAA GATGCTGAAA ACACCGTGGA TACTGCTTCC     300

AAGCCAGGAC TTCAGGAGCG TCTCCAAAAG CATGATATCT CTGAAAGTGT GAACTTCGAT     360

GAGGAGACTG ATGGAATATC CCAGTCAGCA TGTTTAGAAA GACCCAATTC TGCATCAAGC     420

CAGAATTCAA CCGATACAGG CACTTCCGGT TCTGCTACTG CCGCCCAACC AGCTGATAAC     480

CTCCTGGGAG ACATAGACGA CCTGGAGGAC TTTGTGTATA GTCCTGCCCC TCAAGGTGTC     540

ACAGTAAGAT GTCGGATAAT CCGGGATAAA AGGGGAATGG ATCGGGGTCT CTTCCCCACC     600

TACTATATGT ACTTGGAAAA AGAAGAAAAT CAGAAGATAT TTCTTCTTGC AGCTAGAAAG     660

CGGAAAAAGA GCAAAACAGC CAACTACCTT ATCTCCATTG ATCCAGTTGA TTTATCTCGT     720

GAAGGAGAAA GTTATGTCGG CAAGCTTAGA TCCAACCTCA TGGGGACCAA GTTTACAGTT     780

TATGACCGTG GCATCTGCCC CATGAAGGGC CGGGGTTTGG TAGGAGCGGC CCACACCCGG     840

CAGGAGCTGG CTGCCATCTC CTATGTGAGT GCTGCTTTCC CAGGGCCGCT GCCTGCCCTC     900

CTGGTGTCCT GCTGGCACTT TTCACCTAGT GTCGCTGAAG AACTCCCCTC CCAAGCTTGT     960

TTCTATTTCT GTGATTTCTG TTGCTGTACC ATTTTCTCCA TGTATTTGAG TTTTAGTTAT    1020
```

```
TTGAATTGCC AAGTTCAATT ATTTTTCACT CTCAGAACAT TTCTTCCCTT ATTTCCTTTT    1080

CTTTTTTCCT GCTGCCACTT AATTCAGACC TTTACTTCTT ACCCAGTGGC CAAAGGTTAC    1140

AATAAATTAA AGCTGATCTT TTTTTGCTTT TAATCTTTTC                          1180
```

(2) INFORMATION FOR SEQ ID NO:2:

(i) SEQUENCE CHARACTERISTICS:
        (A) LENGTH: 390 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Lys Met Arg Gln Ala Lys Leu Asp Tyr Gln Arg Leu Leu Glu
 1               5                  10                  15

Lys Arg Gln Arg Lys Lys Arg Leu Glu Pro Phe Met Val Gln Pro Asn
                 20                  25                  30

Pro Glu Ala Arg Leu Arg Arg Ala Lys Pro Arg Ala Ser Asp Glu Gln
                 35                  40                  45

Thr Pro Leu Val Asn Cys His Thr Pro His Ser Asn Val Ile Leu His
 50                  55                  60

Gly Ile Asp Gly Pro Ala Ala Val Leu Lys Pro Asp Glu Val His Ala
65                   70                  75                  80

Pro Ser Val Ser Ser Val Val Glu Glu Asp Ala Glu Asn Thr Val
                 85                  90                  95

Asp Thr Ala Ser Lys Pro Gly Leu Gln Glu Arg Leu Gln Lys His Asp
                100                 105                 110

Ile Ser Glu Ser Val Asn Phe Asp Glu Glu Thr Asp Gly Ile Ser Gln
                115                 120                 125

Ser Ala Cys Leu Glu Arg Pro Asn Ser Ala Ser Ser Gln Asn Ser Thr
    130                 135                 140

Asp Thr Gly Thr Ser Gly Ser Ala Thr Ala Ala Gln Pro Ala Asp Asn
145                 150                 155                 160

Leu Leu Gly Asp Ile Asp Asp Leu Glu Asp Phe Val Tyr Ser Pro Ala
                165                 170                 175

Pro Gln Gly Val Thr Val Arg Cys Arg Ile Ile Arg Asp Lys Arg Gly
                180                 185                 190

Met Asp Arg Gly Leu Phe Pro Thr Tyr Tyr Met Tyr Leu Glu Lys Glu
                195                 200                 205

Glu Asn Gln Lys Ile Phe Leu Leu Ala Ala Arg Lys Arg Lys Lys Ser
    210                 215                 220

Lys Thr Ala Asn Tyr Leu Ile Ser Ile Asp Pro Val Asp Leu Ser Arg
225                 230                 235                 240

Glu Gly Glu Ser Tyr Val Gly Lys Leu Arg Ser Asn Leu Met Gly Thr
                245                 250                 255

Lys Phe Thr Val Tyr Asp Arg Gly Ile Cys Pro Met Lys Gly Arg Gly
                260                 265                 270

Leu Val Gly Ala Ala His Thr Arg Gln Glu Leu Ala Ala Ile Ser Tyr
            275                 280                 285

Val Ser Ala Ala Phe Pro Gly Pro Leu Pro Ala Leu Leu Val Ser Cys
    290                 295                 300

Trp His Phe Ser Pro Ser Val Ala Glu Glu Leu Pro Ser Gln Ala Cys
305                 310                 315                 320
```

```
Phe Tyr Phe Cys Asp Phe Cys Cys Cys Thr Ile Phe Ser Met Tyr Leu
                325             330                 335

Ser Phe Ser Tyr Leu Asn Cys Gln Val Gln Leu Phe Phe Thr Leu Arg
            340             345                 350

Thr Phe Leu Pro Leu Phe Pro Phe Leu Phe Ser Cys Cys His Leu Ile
        355             360             365

Gln Thr Phe Thr Ser Tyr Pro Val Ala Lys Gly Tyr Asn Lys Leu Lys
    370             375             380

Leu Ile Phe Phe Cys Phe
385             390
```

(2) INFORMATION FOR SEQ ID NO:3:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCACGAGCT TTTTTCCCAG AGGCTACTAC TTGAGAAGAG GCAAAGGAAA AAGCGCCTTG    60

AGCCATTTAT GGTGCAGCCC AATCCAGAAG CCAGGCTACG TCGGGCAAAG CAAGGGCCAG   120

TGATGAGCAG ACTCCCTTGG GTGAACTGTC ATACTCCCCA CAGCAATGTC ATCTTACATG   180

GTATTGATGG TCCAGCTGCT GTCCTGAAAC CAGACGAAGG TTCATGCTCC ATCAGTAAGC   240

TCTCTGTTGT GGAAGAAGAT GCTGAAAACA CCGTGGATAC TGCTTCCAAG CCAGGACTTC   300

AGGAGCGTCT CCAAAAGCAT GATATCTCTG AAAGTGTGAA CTTCGATGAG GAGACTGATG   360

GAATATCCCA GTCAGCATGT TTAGAAAGAC CCAATTCTGC ATCAAGCCAG AATTCAACCG   420

ATACAGGCAC TTCCGGTTCT GCTACTGCCG CCCAACCAGC TGATAACCTC CTGGGAGACA   480

TAGACGACCT GGAGGACTTT GTGTATAGTC CTGCCCCTCA AGGTGTCACA GTAAGATGTC   540

GGATAATCCG GGATAAAAGG GGAATGGATC GGGGTCTCTT CCCCACCTAC TATATGTACT   600

TGGAAAAAGA AGAAAATCAG AAGATATTTC TTCTTGCAGC TAGAAAGCGG AAAAAGAGCA   660

AAACAGCCAA CTACCTTATC TCCATTGATC CAGTTGATTT ATCTCGTGAA GGANAAAGTT   720

ATGTCGGGG                                                          729
```

(2) INFORMATION FOR SEQ ID NO:4:

(i) SEQUENCE CHARACTERISTICS:
        (A) LENGTH: 242 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
His Glu Leu Phe Ser Gln Arg Leu Leu Glu Lys Arg Gln Arg Lys
  1             5                  10                  15

Lys Arg Leu Glu Pro Phe Met Val Gln Pro Asn Pro Glu Ala Arg Leu
            20              25                  30

Arg Arg Ala Lys Gln Gly Pro Val Met Ser Arg Leu Pro Trp Val Asn
            35              40                  45

Cys His Thr Pro His Ser Asn Val Ile Leu His Gly Ile Asp Gly Pro
        50              55                  60
```

-continued

```
Ala Ala Val Leu Lys Pro Asp Glu Gly Ser Cys Ser Ile Ser Lys Leu
 65              70              75              80

Ser Val Val Glu Glu Asp Ala Glu Asn Thr Val Asp Thr Ala Ser Lys
                 85              90              95

Pro Gly Leu Gln Glu Arg Leu Gln Lys His Asp Ile Ser Glu Ser Val
            100             105             110

Asn Phe Asp Glu Glu Thr Asp Gly Ile Ser Gln Ser Ala Cys Leu Glu
        115             120             125

Arg Pro Asn Ser Ala Ser Ser Gln Asn Ser Thr Asp Thr Gly Thr Ser
    130             135             140

Gly Ser Ala Thr Ala Ala Gln Pro Ala Asp Asn Leu Leu Gly Asp Ile
145             150             155             160

Asp Asp Leu Glu Asp Phe Val Tyr Ser Pro Ala Pro Gln Gly Val Thr
            165             170             175

Val Arg Cys Arg Ile Ile Arg Asp Lys Arg Gly Met Asp Arg Gly Leu
            180             185             190

Phe Pro Thr Tyr Tyr Met Tyr Leu Glu Lys Glu Glu Asn Gln Lys Ile
        195             200             205

Phe Leu Leu Ala Ala Arg Lys Arg Lys Lys Ser Lys Thr Ala Asn Tyr
    210             215             220

Leu Ile Ser Ile Asp Pro Val Asp Leu Ser Arg Glu Gly Xaa Ser Tyr
225             230             235             240

Val Gly
```

TUBBY 2 POLYPEPTIDES

This application claims the benefit of priority of UK patent application number 9624433.0 filed on Nov. 25, 1996, and of European patent application number 97307877.7 filed on Oct. 6, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the Tubby related polypeptides family, hereinafter referred to as Tubby 2. The invention also relates to inhibiting or activating the action of such polynucleotides and polypeptides.

BACKGROUND OF THE INVENTION

The mouse tubby gene has been shown to be mutated in the so-called 'Tubby' mouse model (Kleyn, PW et al (1996) Cell 85, 281–290; Noben-Trauth, K et al. (1996) Nature 380: 534–538). Mutant mice exhibit weight gain from age 6 months and develop insulin resistance associated with this weight gain. There is also evidence of increased susceptibility to atherosclerosis and dyslipidemia in these mutant mice. Kleyn et al. also describe the human orthologue of the mouse tubby gene. It is suggested that changes in the tubby polypeptide are relevant to human weight gain disorders. Kleyn et al however provide no description of the biochemical or signalling properties of the tubby protein.

International patent application, publication number WO 96/05861, relates to compositions and methods for the treatment of bodyweight disorders and in particular identifies certain genes which are used in these composition and methods.

There is a need for identification and characterization of further members of the Tubby related polypeptides family which can play a role in preventing, ameliorating or correcting dysfunctions or diseases.

SUMMARY OF THE INVENTION

In one aspect, the invention relates to Tubby 2 polypeptides and recombinant materials and methods for their production. Another aspect of the invention relates to methods for using such Tubby 2 polypeptides and polynucleotides. Such uses include the treatment of diabetes, obesity, and atherosclerosis, among others. In still another aspect, the invention relates to methods to identify agonists and antagonists using the materials provided by the invention, and treating conditions associated with Tubby 2 imbalance with the identified compounds. Yet another aspect of the invention relates to diagnostic assays for detecting diseases associated with inappropriate Tubby 2 activity or levels.

DESCRIPTION OF THE INVENTION

Polypeptides of the Invention

In a first aspect, the present invention relates to Tubby 2 polypeptides and variants and fragments thereof. Such polypeptides include isolated polypetides comprising an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:2. Such polypeptides include those comprising the amino acid of SEQ ID NO:2.

Tubby 2 polypeptides also include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

The Tubby 2 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the Tubby 2 polypeptides are also included in the invention. A fragment is a polypeptide having an amino acid sequence that entirely is the same as part, but not all, of the amino acid sequence of the aforementioned Tubby 2 polypeptides. As with Tubby 2 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of Tubby 2 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of Tubby 2 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate Tubby 2 activity, including those with a similar activity or an improved activity, or with a decreased undesirable activity. Also included are those that are antigenic or immunogenic in an animal, especially in a human.

Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The Tubby 2 polypeptides of the invention can be prepared in any suitable manner. Such polypeptides include isolated naturally occurring polypeptides, recombinantly produced polypeptides, synthetically produced polypeptides, or polypeptides produced by a combination of

Polynucleotides of the Invention

In a further aspect, the present invention relates to Tubby 2 polynucleotides. Such polynucleotides include isolated polynucleotides comprising a nucleotide sequence which has at least 70% identity, preferably at least 80% identity, more preferably at least 90% identity, yet more preferably at least 95% identity, to a nucleotide sequence encoding the polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Tubby 2 polynucleotides further includes isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identiy are more highly preferred, and those with at least 99% identity are most highly preferred. Such polynucleotides include a polynucleotide which is the olynucleotide of SEQ ID NO:1.

The invention also provides polynucleotides which are complementary to such polynucleotides.

Tubby 2 of the invention is structurally related to other proteins of the Tubby related polypeptides family, as shown by the results of sequencing the cDNA encoding human Tubby 2. The cDNA sequence of SEQ ID NO:1 contains an open reading frame (nucleotide number 1 to 1170) encoding a polypeptide of 390 amino acids of SEQ ID NO:2. Amino acid sequence of Table 1 (SEQ ID NO:2) has about 60% identity (using BlastX) in 266 amino acid residues with Tubby [(P50586) Kleyn, PW, et al, Cell 1996 Apr. 19, 1985(2):281–290]. Nucleotide sequence of Table 1 (SEQ ID NO:1) has about 60% identity (using BlastN) in 371 nucleotide residues with Mus musculus tubby candidate (tub) mRNA [(U52824) Kleyn, PW, et al, Cell 1996 Apr. 19, 1985(2):281–290]. There is found to be significant conservation of the dibasic potential protease cleavage sequences between tubby and the Tubby 2 polypeptide (amino acids 302 and 383, Kleyn et al) which indicate that the Tubby 2 polypeptide could be cleaved in vivo into smaller active peptide(s). There is however lower similarity towards the 5' end (amino acids 167–202, Kleyn at al.), suggesting that there may be important functional differences between tubby and the Tubby 2 polypeptide.

TABLE 1[a]

| | |
|---|---|
| 1 | ATGAAGATGC GACaGGCTAA GCTGGATTAT CAGAGGCTAC TACTTGAGAA |
| 51 | GAGGCAAAGG AAAAAGCGCC TTGAGCCATT TATGGTGCAG CCCAATCCAG |
| 101 | AAGCCAGGCT ACGTCGGGCA AAGCcAAGGG CCAGTGATGA GCAGACTCCC |
| 151 | TTGGTGAACT GTCATACTCC CCACAGCAAT GTCATCTTAC ATGGTATTGA |
| 201 | TGGTCCAGCT GCTGTCCTGA AACCAGACGA AGTTCATGCT CCATCAGTAA |
| 251 | GCTCcTCTGT TGTGGAAGAA GATGCTGAAA ACACCGTGGA TaCTGCTTCC |
| 301 | AAGCCAGGAC TTCAGGAGCG TCTCCAAAAG CATGATATCT CTGAAAGTGT |
| 351 | GAACTTCGAT GAgGAGACTG ATGGAATATC CCAGTCAGCA TGTTTAGAAA |
| 401 | GACCCAATTC TGCATCAAGC CAGAATTCAA CCGATACAGG CACTTCCGGT |
| 451 | TCTGCTACTG CCGCCCAACC AGCTGATAAC cTCCTGGGAG ACATAGACGA |
| 501 | CCTGGAGGAC TTTGTGTATA GTCCTGCCCc TCAAGGTGTC ACAGTAAGAT |
| 551 | GTCGGATAAT CCGGGATAAA AGGGGAATGG ATCGGGTCT CTTCCCCACC |
| 601 | TACTATATGT ACTTGGAAAA AGAAGAAAAT CAGAAGATAT TTCTTCTTGC |
| 651 | AGCTAGAAAG CGGAAAAAGA GCAAAACAGC CAACTACcTT ATcTCCATtG |
| 701 | ATCCAGTTGA TTTATcTCGT GAAGGAGAAA GTTATGTCGG CAAGCTTAGA |
| 751 | TCCAACCTCA TGGGGACCAA GTTTACAGTT TATGACCGTG GCATCTGCCC |
| 801 | CATGAAGGGC CGGGGTTTGG TAGGAGCGGC CCACACCCGG CAGGAGCTGG |
| 851 | CTGCCATCTC CTATGTGAGT GCTGCTTTCC CAGGGCCGCT GCCTGCCCTC |
| 901 | CTGGTGTCCT GCTGGCACTT TTCACCTAGT GTCGCTGAAG AACTCCCCTC |
| 951 | CcAAGCTTGT TTCTATTTCT GTGATTTCTG TTGCTGTACC ATTTTCTCCA |
| 1001 | TGTATTTGAG TTTTAGTTAT TTGAATTGCC AAGTTCAATT ATTTTTCACT |

TABLE 1ᵃ-continued

| | | | | |
|---|---|---|---|---|
| 1051 | CTCAGAACAT | TTCTTCCCTT | ATTTCCTTTT | CTTTTTTCCT GCTGCCACTT |
| 1101 | AATTCAGACC | TTTACTTCTT | ACCCAGTGGC | CAAAGGTTAC AATAAATTAA |
| 1151 | AGCTGATCTT | TTTTTGCTTT | TAATCTTTTC | |

ᵃA nucleotide sequence of a human Tubby 2 (SEQ ID NO: 1)

TABLE 2ᵇ

| | | | | |
|---|---|---|---|---|
| 1 | MKMRQAKLDY | QRLLLEKRQR | KKRLEPFMVQ | PNPEARLRRA KPRASDEQTP |
| 51 | LVNCHTPHSN | VILHGIDGPA | AVLKPDEVHA | PSVSSSVVEE DAENTVDTAS |
| 101 | KPGLQERLQK | HDISESVNFD | EETDGISQSA | CLERPNSASS QNSTDTGTSG |
| 151 | SATAAQPADN | LLGDIDDLED | FVYSPAPQGV | TVRCRIIRDK RGMDRGLFPT |
| 201 | YYMYLEKEEN | QKIFLLAARK | RKKSKTANYL | ISIDPVDLSR EGESYVGKLR |
| 251 | SNLMGTKFTV | YDRGICPMKG | RGLVGAAHTR | QELAAISYVS AAFPGPLPAL |
| 301 | LVSCWHFSPS | VAEELPSQAC | FYFCDFCCCT | IFSMYLSFSY LNCQVQLFFT |
| 351 | LRTFLPLFPF | LFSCCHLIQT | FTSYPVAKGY | NKLKLIFFCF LNCQVQLFFT |

ᵇAn amino acid sequence of a human Tubby 2 (SEQ ID NO: 2)

One polynucleotide of the present invention encoding Tubby 2 may be obtained using standard cloning and screening, from a cDNA library derived from mRNA in cells of human Substantia Nigra using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding Tubby 2 polypeptide of SEQ ID NO:2 may be identical to the polypeptide encoding sequence contained in Table 1 (nucleotide number 1 to 1170 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of Tubby 2 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag.

The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding Tubby 2 variants comprising the amino acid sequence of Tubby 2 polypeptide of Table 2 (SEQ ID NO:2) in which several, 5–10, 1–5, 1–3, 1–2 or 1 amino acid residues are substituted, deleted or added, in any combination.

The programme of work leading to the determination of SEQ ID NO:1 and 2 started with the preliminary identification of shorter length gene fragments (ESTs). Accordingly, in a further aspect, the present invention provides for a Tubby 2 characterised by the deduced amino acid sequence of SEQ ID NO:4; or a fragment thereof, and for polynucleotides which encode such polypeptides, in particular, the polynucleotide comprising the partial DNA sequence given in SEQ ID NO:3. In further aspects, the present invention provides for the polynucleotide of SEQ ID NO:3 encoding the amino acid sequence of SEQ ID NO:4, the polynucloetide which has the sequence given in SEQ ID NO:3 and the polypeptide which has the amino acid sequence of SEQ ID NO:4. It will be readily appreciated that the polynucleotide of SEQ ID NO:3 and the polypeptide of SEQ ID NO:3 may be described as fragments of the polynucleotide of SEQ ID NO:1 and the polypeptide of SEQ ID NO:2, respectively. In references herein to SEQ ID NO:1, SEQ ID NO:1 may be replaced by SEQ ID NO:3 and in references herein to SEQ ID NO:2, SEQ ID NO:2 may be replaced by SEQ ID NO:4.

TABLE 3ᶜ ggcacgagcttttttcccagaggctactacttgagaagaggcaaaggaaaaagcgccttgagccatttatggtgcagccc aatccagaagccaggctacgtcgggcaaagcaagggccagtgatgagcagactcccttgggtgaactgtcatactcccca cagcaatgtcatcttacatggtattgatggtccagctgctgtcctgaaaccagacgaaggttcatgctccatcagtaagc TABLE 3^c-continued tctctgttgtggaagaagatgctgaaaacaccgtggatactgcttccaagccaggacttcaggagcgtctccaaaagcat gatatctctgaaagtgtgaacttcgatgaggagactgatggaatatcccagtcagcatgtttagaaagacccaattctgc atcaagccagaattcaaccgatacaggcacttccggttctgctactgccgcccaaccagctgataacctcctgggagaca tagacgacctggaggactttgtgtatagtcctgccctcaaggtgtcacagtaagatgtcggataatccgggataaaagg ggaatggatcgggtctcttccccacctactatatgtacttggaaaaagaagaaaatcagaagatatttcttcttgcagc tagaaagcggaaaaagagcaaaacagccaactaccttatctccattgatccagttgatttatctcgtgaagganaaagtt atgtcgggg ^c A partial nucleotide sequence of a human Tubby 2 (SEQ ID NO: 3)

TABLE 4^d

HELFSQRLLLEKRQRKKRLEPFMVQPNPEARLRRAKQGPVMSRLPWVNCHTP

HSNVILHGIDGPAAVLKPDEGSCSISKLSVVEEDAENTVDTASKPGLQERLQK

HDISESVNFDEETDGISQSACLERPNSASSQNSTDTGTSGSATAAQPADNLLG

DIDDLEDFVYSPAPQGVTVRCRIIRDKRGMDRGLFPTYYMYLEKEENQKIFLL

AARKRKKSKTANYLISIDPVDLSREGXSYVG

^d A partial amino acid sequence of a human Tubby 2 (SEQ ID NO: 4)

Whilst the polynucleotide of SEQ ID NO:3 does not include a full open reading frame, a full length clone can readily be obtained by methods well known to persons skilled in the art. Among the alternative methods of choice, the following examples shuold be mentioned: 1) The human library type cDNA library can either be rescreened with a probe from the 5' end of the already cloned sequence, 2) Anchor-PCR or RACE (Rapid Amplificaiton of cDNA Ends) (Kriangkum et al., Nucleic Acids Res. 20 (1992) 3793–3794: Troutt et al., Proc. Natl Acad. Sci., USA 89 (1992), 9823 –9825) methodoloy can be used to clone the remaining 5' seqeuences from Tissue Type RNA.3). The remaining 5' part can be isolated from human genomic libraries, and DNA fragments considred to represent introns can be identified on homology to the cDNA of the rat receptor and deleted by mutagenesis.

After cloning of the 5' end for the open reading frame, this part of the cDNA can be fused to the remaining 3' part of the human T2 polypeptide cDNA by the use of PCR or through fusion at appropriate restriction enzyme recognition seqeuences identied in both the 5' and the 3' parts.

The cDNA encoding the full length open reading frame can be cloned in suitable mammalian expression vectors and transfected into mammalian cell lines for expression. Examples of such suitable cell lines are the CHO and CHL cells, but other mammalian cells will also express receptors o this type.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding Tubby 2 polypeptide and to isolate cDNA and genomic clones of other genes (including genes encoding homologs and orthologs from species other than human) that have a high sequence similarity to the Tubby 2 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding Tubby 2 polypeptide, including homologs and orthologs from species other than human, comprises the steps of screening an appropriate library under stingent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art. Thus in another aspect, Tubby 2 polynucleotides of the present invention further include a nucleotide sequence comprising a nucleotide sequence that hybridize under stringent conditions to a nucleotide sequence having SEQ ID NO:1 or a fragment thereof (including that of SEQ ID NO:3). Also included with Tubby 2 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY(1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the Tubby 2 polypeptide is to be expressed for use in screening assays, generally, it is preferred that the polypeptide be produced at the surface of the cell. In this event, the cells may be harvested prior to use in the screening assay. If Tubby 2 polypeptide is secreted into the medium, the medium can be recovered in order to recover and purify the polypeptide; if produced intracellularly, the cells must first be lysed before the polypeptide is recovered. Tubby 2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of Tubby 2 polynucleotides for use as diagnostic reagents. Detection of a mutated form of Tubby 2 gene associated with a dysfunction will provide a diagnostic tool that can add to or define a diagnosis of a disease or susceptibility to a disease which results from under-expression, over-expression or altered expression of Tubby 2. Individuals carrying mutations in the Tubby 2 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Tubby 2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et aL, Science (1985) 230:1242. Sequence changes at specific locations may also be revealed by nuclease protection assays, such as RNase and S1 protection or the chemical cleavage method. See Cotton et al., Proc Natl Acad Sci USA (1985) 85: 4397–4401. In another embodiment, an array of oligonucleotides probes comprising Tubby 2 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et aL, Science, Vol 274, pp 610–613 (1996)).

The diagnostic assays offer a process for diagnosing or determining a susceptibility to diabetes, obesity, and atherosclerosis through detection of mutation in the Tubby 2 gene by the methods described.

In addition, diabetes, obesity, and atherosclerosis can be diagnosed by methods comprising determining from a sample derived from a subject an abnormally decreased or increased level of Tubby 2 polypeptide or Tubby 2 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an Tubby 2 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly diabetes, obesity, and atherosclerosis, which comprises:

(a) a Tubby 2 polynucleotide, preferably the nucleotide sequence of SEQ ID NO:1, or a fragment thereof;

(b) a nucleotide sequence complementary to that of (a);

(c) a Tubby 2 polypeptide, preferably the polypeptide of SEQ ID NO:2, or a fragment thereof, or (d) an antibody to a Tubby 2 polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

The Tubby 2 gene has been mapped to chromosome 12p13.3.

Antibodies

The polypeptides of the invention or their fragments or analogs thereof, or cells expressing them can also be used as immunogens to produce antibodies immunospecific for the Tubby 2 polypeptides. The term "immunospecific" means that the antibodies have substantiall greater affinity for the polypeptides of the invention than their affinity for other related polypeptides in the prior art.

Antibodies generated against the Tubby 2 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against Tubby 2 polypeptides may also be employed to treat diabetes, obesity, and atherosclerosis, among others.

Vaccines

Another aspect of the invention relates to a method for inducing an immunological response in a mammal which comprises inoculating the mammal with Tubby 2 polypeptide, or a fragment thereof, adequate to produce antibody and/or T cell immune response to protect said animal from diabetes, obesity, and atherosclerosis, among others. Yet another aspect of the invention relates to a method of inducing immunological response in a mammal which comprises, delivering Tubby 2 polypeptide via a vector directing expression of Tubby 2 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a Tubby 2 polypeptide wherein the composition comprises a Tubby 2 polypeptide or Tubby 2 gene. The vaccine formulation may further comprise a suitable carrier. Since Tubby 2 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine fonnulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The Tubby 2 polypeptide of the present invention may be employed in a screening process for compounds which activate (agonists) or inhibit activation of (antagonists, or otherwise called inhibitors) the Tubby 2 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

Tubby 2 polypeptides are responsible for many biological functions, including many pathologies. Accordingly, it is desirous to find compounds and drugs which stimulate Tubby 2 polypeptide on the one hand and which can inhibit the function of Tubby 2 polypeptide on the other hand. In general, agonists are employed for therapeutic and prophylactic purposes for such conditions as Diabetes, obesity, atherosclerosis. Antagonists may be employed for a variety of therapeutic and prophylactic purposes for such conditions as diabetes, obesity, and atherosclerosis.

In general, such screening procedures may involve using appropriate cells which express the Tubby 2 polypeptide or respond to Tubby 2 polypeptide of the present invention. Such cells include cells from mammals, yeast, Drosophila or E. coli. Cells which express the Tubby 2 polypeptide (or cell membrane containing the expressed polypeptide) or respond to Tubby 2 polypeptide are then contacted with a test compound to observe binding, or stimulation or inhibition of a functional response. The ability of the cells which were contacted with the candidate compounds is compared with the same cells which were not contacted for Tubby 2 activity.

The assays may simply test binding of a candidate compound wherein adherence to the cells bearing the Tubby 2 polypeptide is detected by means of a label directly or indirectly associated with the candidate compound or in an assay involving competition with a labeled competitor. Further, these assays may test whether the candidate compound results in a signal generated by activation of the Tubby 2 polypeptide, using detection systems appropriate to the cells bearing the Tubby 2 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a Tubby 2 polypeptide to form a mixture, measuring Tubby 2 activity in the mixture, and comparing the Tubby 2 activity of the mixture to a standard.

The Tubby 2 cDNA, protein and antibodies to the protein may also be used to configure assays for detecting the effect of added compounds on the production of Tubby 2 mRNA and protein in cells. For example, an ELISA may be constructed for measuring secreted or cell associated levels of Tubby 2 protein using monoclonal and polyclonal antibodies by standard methods known in the art, and this can be used to discover agents which may inhibit or enhance the production of Tubby 2 (also called antagonist or agonist, respectively) from suitably manipulated cells or tissues.

The Tubby 2 protein may be used to identify membrane bound or soluble receptors, if any, through standard receptor binding techniques known in the art. These include, but are not limited to, ligand binding and crosslinking assays in which the Tubby 2 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of Tubby 2 which compete with the binding of Tubby 2 to its receptors, if any. Standard methods for conducting screening assays are well understood in the art.

Examples of potential Tubby 2 polypeptide antagonists include antibodies or, in some cases, oligonucleotides or proteins which are closely related to the ligands, substrates, enzymes, receptors, etc., as the case may be, of the Tubby 2 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for Tubby 2 polypeptides; or compounds which decrease or enhance the production of Tubby 2 polypeptides, which comprises:

(a) a Tubby 2 polypeptide, preferably that of SEQ ID NO:2;

(b) a recombinant cell expressing a Tubby 2 polypeptide, preferably that of SEQ ID NO:2;

(c) a cell membrane expressing a Tubby 2 polypeptide; preferably that of SEQ ID NO:2; or (d) antibody to a Tubby 2 polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, Diabetes, obesity, atherosclerosis, related to both an excess of and insufficient amounts of Tubby 2 polypeptide activity.

If the activity of Tubby 2 polypeptide is in excess, several approaches are available. One approach comprises administering to a subject an inhibitor compound (antagonist) as hereinabove described along with a pharmaceutically acceptable carrier in an amount effective to inhibit the function of the Tubby 2 polypeptide, such as, for example, by blocking the binding of ligands, substrates, enzymes, receptors, etc., or by inhibiting a second signal, and thereby alleviating the abnormal condition. In another approach, soluble forms of Tubby 2 polypeptides still capable of binding the ligand, substrate, enzymes, receptors, etc. in competition with endogenous Tubby 2 polypeptide may be administered. Typical embodiments of such competitors comprise fragments of the Tubby 2 polypeptide.

In another approach, soluble forms of Tubby 2 polypeptides still capable of binding the ligand in competition with endogenous Tubby 2 polypeptide may be administered. Typical embodiments of such competitors comprise fragments of the Tubby 2 polypeptide.

In still another approach, expression of the gene encoding endogenous Tubby 2 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administeredper se or the relevant oligomers can be expressed in vivo.

For treating abnormal conditions related to an under-expression of Tubby 2 and its activity, several approaches are also available. One approach comprises administering to a subject a therapeutically effective amount of a compound which activates Tubby 2 polypeptide, i.e., an agonist as described above, in combination with a pharmaceutically acceptable carrier, to thereby alleviate the abnormal condition. Alternatively, gene therapy may be employed to effect the endogenous production of Tubby 2 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of Tubby 2 polypeptides in combination with a suitable pharmaceutical carrier.

Formulation and Administration

Peptides, such as the soluble form of Tubby 2 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

This invention also provides a transgenic non-human animal comprising a T2 polynucleotide encoding a T2 polypeptide. Also provided are methods for use of said transgenic animals as models for mutation and SAR (structure/activity relationship) evaluation as well as in drug screens.

Definitions

The following definitions are provided to facilitate understanding of certain terms used frequently hereinbefore.

"Tubby 2 activity or Tubby 2 polypeptide activity" or "biological activity of the Tubby 2 or Tubby 2 polypeptide" refers to the metabolic or physiologic function of said Tubby 2 including similar activities or improved activities or these activities with decreased undesirable side-effects. Also included are antigenic and immunogenic activities of said Tubby 2.

"Tubby 2 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A.M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART 1, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

All publications, including but not limited to patents and patent applications, cited in this specification are herein incorporated by reference as if each individual publication were specifically and individually indicated to be incorporated by reference herein as though fully set forth.

EXAMPLE

An EST sequence (Human Genome Sciences, HGS 160391 1) was identified as having homology with the published human and mouse tubby gene sequences (Kleyn et al 1996). Further ESTs with the same project ID (HSXAK37) from a substantia nigra cDNA library were identified as derived from the more 5' region of the novel Tubby 2 gene. Oligos were designed in each of the non-overlapping EST sequences and PCR between these non-overlapping sequences was performed and the resulting products cloned and sequenced. The set of HGS plus SB generated sequences were combined to create the polynucleotide (SEQ ID NO 3) and the deduced polypeptide (SEQ ID NO 4).

The template for this PCR was Clontech Foetal Brain cDNA in lambda gt 11 vector (Clontech Laboratories inc., 4030 Fabian Way, Palo Alto, Calif. 94303-40607, USA). PCR reaction conditions were 94° C. for 45 seconds, 60° C. for 45 seconds, 72° C. for 2 minutes, 35 cycles in an MJ PTC-100 thermal cycler.

Expression profiles were determined using the same primers and conditions as above on the Clontech Quickscreen panel.

The Chromosomal localisation of the Tubby 2 gene was determined using oligos Tb3 and Tb4 on the GeneBridge 4 radiation hybrid panel (Research Genetics, USA) using the conditions: 94° C. for 40 seconds, 65° C. for 30 seconds, 35 cycles on the MJ PTC-100 thermal cycler. This has positioned the Tubby 2 polypeptide on chromosome 12P13.

What is claimed is:

1. An isolated polypeptide comprising an amino acid sequence which has at least 70% identity to the amino acid sequence of SEQ ID NO:2 over the entire length of SEQ ID NO:2, said identity being calculated using FASTA wherein the two sequences are aligned so that highest order match is obtained.

2. An isolated polypeptide as claimed in claim 1 in which the amino acid sequence has at least 80% identity, said identity being calculated using FASTA wherein the two sequences are aligned so that highest order match is obtained.

3. An isolated polypeptide as claimed in claim 1 in which the amino acid sequence has at least 90% identity, said identity being calculated using FASTA wherein the two sequences are aligned so that highest order match is obtained.

4. An isolated polypeptide comprising the amino acid sequence of SEQ ID NO:2.

5. The isolated polypeptide of claim 4 consisting essentially of the amino acid sequence of SEQ ID NO:2.

6. An isolated polypeptide comprising the amino acid sequence of SEQ ID NO:4.

7. The polypeptide of claim 6 consisting essentially of the amino acid sequence of SEQ ID NO:4.

8. An isolated polypeptide comprising at least 50 contiguous amino acids from the amino acid sequence set forth in SEQ ID NO:2.

9. The isolated polypeptide of claim 8 comprising at least 100 contiguous amino acids from the amino acid sequence set forth in SEQ ID NO:2.

10. The isolated polypeptide of claim 8 comprising at least 200 contiguous amino acids from the amino acid sequence set forth in SEQ ID NO:2.

11. The isolated polypeptide of claim 8 comprising at least 300 contiguous amino acids from the amino acid sequence set forth in SEQ ID NO:2.

12. An isolated polypeptide comprising at least 50 contiguous amino acids from the amino acid sequence set forth in SEQ ID NO:4.

13. The isolated polypeptide of claim 12 comprising at least 100 contiguous amino apids from the amino acid sequence set forth in SEQ ID NO:4.

14. The isolated polypeptide of claim 12 comprising at least 200 contiguous amino acids from the amino acid sequence set forth in SEQ ID NO:4.

* * * * *